United States Patent [19]

Taranto et al.

[11] Patent Number: 5,651,774
[45] Date of Patent: Jul. 29, 1997

[54] HYPODERMIC SYRINGE WITH SAFETY SHIELD AND METHOD OF USING SAME

[75] Inventors: William J. Taranto, 1401 W. Paces Ferry Rd., No. 5403, Atlanta, Ga. 30327; Norman C. Maarschalkerweerd, Roswell, Ga.

[73] Assignee: William J. Taranto, Atlanta, Ga.

[21] Appl. No.: 712,314

[22] Filed: Sep. 11, 1996

[51] Int. Cl.$^6$ .................................................. A61M 5/32
[52] U.S. Cl. .......................... 604/198; 604/111; 604/263
[58] Field of Search ................................. 604/111, 187, 604/192, 198, 263, 207, 116, 117

[56] References Cited

U.S. PATENT DOCUMENTS

| | | | |
|---|---|---|---|
| D. 344,355 | 2/1994 | Talonn et al. | D24/112 |
| 3,820,541 | 6/1974 | Langan | 128/215 |
| 4,139,009 | 2/1979 | Alvarez | 128/218 |
| 4,232,669 | 11/1980 | Nitshke | 128/218 |
| 4,273,123 | 6/1981 | Lemelson | 128/218 |
| 4,743,233 | 5/1988 | Schneider | 604/192 |
| 4,874,383 | 10/1989 | McNaughton | 604/198 |
| 5,024,660 | 6/1991 | McNaughton | 604/110 |
| 5,053,018 | 10/1991 | Talonn et al. | 604/198 |
| 5,088,988 | 2/1992 | Talonn et al. | 604/198 |
| 5,127,910 | 7/1992 | Talonn et al. | 604/198 |
| 5,147,326 | 9/1992 | Talonn et al. | 604/198 |
| 5,156,599 | 10/1992 | Ranford et al. | 604/198 |
| 5,160,326 | 11/1992 | Talonn et al. | 604/198 |
| 5,169,392 | 12/1992 | Ranford et al. | 604/198 |
| 5,217,437 | 6/1993 | Talonn et al. | 604/198 |
| 5,312,370 | 5/1994 | Talonn et al. | 604/198 |
| 5,324,264 | 6/1994 | Whitaker | 604/111 X |
| 5,352,208 | 10/1994 | Robinson | 604/111 X |
| 5,403,287 | 4/1995 | Talonn et al. | 604/198 |
| 5,496,288 | 3/1996 | Sweeney | 604/263 |
| 5,522,812 | 6/1996 | Talonn et al. | 604/198 |

*Primary Examiner*—John D. Yasko
*Attorney, Agent, or Firm*—Isaf, Vaughan & Kerr; Charles H. Fails

[57] ABSTRACT

An improved hypodermic syringe (5) with safety shield, and method of using same, is disclosed. The hypodermic syringe has an elongate hollow cylindrical barrel (7) with a grip flange (11) formed at a first end (8) thereof, and a hypodermic needle (12) attached to a second end (9) thereof, and in fluid communication with the hollow interior of the barrel. The syringe is provided with a reciprocable plunger assembly (15). An elongate hollow cylindrical safety shield (20) is positioned coaxially about the barrel in a retracted position so that the needle projects axially out of the safety shield for use. The safety shield is constructed and arranged for movement on the barrel from the retracted position into an extended position in which the needle is housed within the safety shield. The safety shield has an integral end shield (36) which can be moved into a closed position transverse to the length of the safety shield for fully enclosing the needle within the safety shield. A series of spaced indicia (4) are marked along at least a portion of the length of the safety shield for use in measuring the amount of fluid drawn through the hypodermic needle and into the hollow interior of the barrel.

26 Claims, 5 Drawing Sheets

HYPODERMIC SYRINGE WITH SAFETY SHIELD AND METHOD OF USING SAME

FIELD OF THE INVENTION

This invention relates in general to hypodermic syringes used for giving injections. More particularly, this invention relates to a hypodermic syringe having a safety shield positioned coaxially about the barrel of the syringe, the safety shield being movable from a retracted position into an extended position for housing the hypodermic needle of the syringe therewithin after use, the safety shield also having a spaced series of indicia marked along at least a portion of the length thereof for use in measuring the fluid drawn into the barrel.

BACKGROUND OF THE INVENTION

Hypodermic syringes have long been in use, and have proven to be an invaluable tool in the prevention and treatment of illness. Due to the use of hypodermic syringes in the treatment of illness, however, and in particular blood related diseases, the need for a hypodermic syringe which can be safely disposed of after use has become increasingly important.

A large portion of the syringes manufactured and sold today are disposable items intended for a single use, after which the syringe is to be disposed of in a safe manner. The conventional disposable hypodermic syringe has a barrel with a first open end and a closed second end, a hypodermic needle extending from the second end and being in fluid communication with the barrel, and a plunger assembly inserted through the open end of the barrel and reciprocable therein for use in drawing fluid through the hypodermic needle and into the barrel, and for forcing fluid from the barrel through the hypodermic needle when giving an injection, for example.

These known disposable hypodermic syringes also include a protective cap or sheath received over the needle and removably secured to the second end of the barrel. After use of the hypodermic syringe, the preferred method of disposal was to place the cap back over the needle on the second end of the syringe barrel, and place the syringe in an appropriate biomedical waste receptacle, or other suitable receptacle provided therefor. However, the placement of the cap back on the second end of the syringe and over the needle requires extreme caution in order to prevent an accidental needle stick in the hand of the person placing the cap back on the syringe. In light of the variety of blood borne illnesses being treated today, to include Hepatitis, and Auto-Immune Disease Syndrome (AIDS), a safer syringe was needed which would prevent accidental needle sticks during handling after use and prior to disposal.

Thus, syringes were developed which had a protective sheath provided coaxially about the barrel of the syringe and movable from a retracted position in which the needle extended or projected from the shield for use, into an extended or locked position in which the shield was moved at least partially about the needle to minimize the risk of accidental needle sticks during handling after use, and in disposal. Numerous hypodermic syringes using safety shields have been developed, among which are those disclosed in U.S. Pat. No. 4,743,233 to Schneider, U.S. Pat. No. 4,874,383 to McNaughton, and in U.S. Pat. No. 5,053,018 to Talonn, et al.

In the patent to Schneider, a safety cap syringe is disclosed which has slidable sleeve positioned on the syringe barrel which is threaded at both of its ends, the second end of the barrel at which the needle is located having a corresponding thread so that the safety cap can be threadably held in an open or retracted position on the barrel. Although Schneider provides a safety cap syringe having a shield movable between a retracted and extended position for at least partially enclosing the needle after use, the patent to Schneider requires that a health professional, or other syringe user, for example, a diabetic, grasp the barrel of the syringe with the fingers of one hand while using the fingers of the other hand to rotate the slidable sleeve for unthreading it from its retracted position, sliding the sleeve forward on the barrel, and then rotating the barrel so that it is threaded into its extended position on the barrel. While preforming these steps, however, the possibility of an accidental needle stick is present, particularly, for example, if the person's hand should slip while trying to rotate and move the sleeve on the syringe.

McNaughton discloses a syringe shield locked in a retracted position on the barrel of the syringe by threads, an elongate guide formed in the barrel of the syringe and having a protrusion extending inwardly from the syringe shield and received therein for guiding the syringe shield along the barrel into the extended position, and a catch or recess for receiving the protrusion to lock the shield into a closed position on the end of the barrel and extending about the needle. Again, and as with the patent to Schneider, after use, the fingers of a person must grasp the barrel of the syringe while the fingers of the other hand are used to once again rotate the barrel, in this instance through a partial quarter turn, then move the shield on the barrel into the extended position, and then once again rotate the shield into a locked position. As with the safety cap syringe of Schneider, therefore, the possibility thus exists that an accidental hand slip or other miscue could result in an accidental needle stick.

Talonn et al. disclose in their patent a combined syringe and needle shield, and a method of manufacture, which once again provides a safety syringe with a needle shield which is movable between a retracted position into an extended position for at least partially enclosing the needle of the syringe after use. To use the syringe of Talonn et al., the needle shield is moved from a retracted position over a series of detents while simultaneously guiding three spaced keys in matched corresponding keyways along the barrel to position the needle shield about the needle. The user then forces the shield into an extended position over a series of stops formed in the collar of the syringe, whereupon the user then grasps the shield and rotates it to lock a spaced series of protrusions formed on the end of the needle shield into a spaced series of slots provided on the collar positioned with respect to the second end of the hypodermic syringe barrel.

Again, and as with the patents to Schneider and McNaughton, the device of Talonn et al. requires that after use of the syringe a person must grasp the barrel of the syringe with the fingers of one hand, grasp the needle shield with the fingers of the second hand, move the needle shield into the extended position, and then rotate the needle shield and ensure that the needle shield clicks or locks into a closed position to ensure that accidental needle sticks are prevented.

None of the patents to Schneider, McNaughton, nor Talonn et al. disclose a needle shield having a cap or end seal formed as an integral part thereof, and which could be moved into a closed position to fully enclose the needle within the safety shield once the safety shield has been moved into its extended or locked position about the needle, thus ensuring that the needle is completely isolated therewithin to prevent the accidental needle stick resulting from a child or other person placing their finger through the otherwise open end of the needle shield and engaging the hypodermic needle therewithin. Moreover, each of the patents to Schneider, McNaughton, and Talonn et al. use a conventional syringe in which a series of indicia or markings are spaced along at least a portion of the length of the barrel for use in measuring the mount of fluid drawn through the hypodermic needle into the barrel of the syringe, i.e., to determine dosage and the like. Thus, the problem arises that the safety shield or needle shield may very well obscure a significant portion of these markings on the barrel of the syringe, or the safety shield must be specially manufactured to allow a health professional or other syringe user to peer through the needle shield to observe the markings on the barrel while also drawing fluid into the barrel, for example a dosage from a vaccine bottle, or blood from a patient, all of which is ordinarily difficult enough without the added distraction of trying to read obscured markings on the barrel of the syringe.

What is needed therefore, but seemingly unavailable in the art, is a hypodermic syringe with a safety shield which can be used quickly and easily in a single one step operation without requiring the unnecessary handling, i.e., rotation of the safety shield while moving the shield into its extended and locked position. What is also needed is an improved hypodermic syringe which is adapted for ease of use as a syringe prior to the time the safety shield is moved into its extended position, and which fully encloses the needle within the safety shield to eliminate the possibility of accidental needle sticks.

SUMMARY OF THE INVENTION

The present invention provides an improved hypodermic syringe with a safety shield, and method of using same, which overcomes some of the design deficiencies of the known art. The improved hypodermic syringe with safety shield of this invention allows greater ease of use, and thus flexibility, in order to help ensure that accurate dosages are injected, or accurate specimens are withdrawn, through the hypodermic syringe. This improved syringe also allows for the complete sealing or closure of the safety shield about the hypodermic needle of the syringe after use to eliminate the possibility of accidental needle sticks or the possibility of contamination due to contact with the needle.

Accordingly, the improved hypodermic syringe with safety shield of this invention includes an elongated hollow cylindrical barrel having a first open end and a spaced second closed end, a grip flange formed at the first end of the barrel, and a hypodermic needle attached to the second end of the barrel and extending axially away therefrom, the needle being in communication with the hollow interior of the barrel, and a reciprocable plunger assembly received within the barrel. An elongated hollow cylindrical safety shield is positioned coaxially about, and on, the barrel in a retracted position so that the needle projects out of the safety shield for use. The safety shield is constructed and arranged for movement on the barrel from the retracted position into an extended position in which the needle is housed within the safety shield. The barrel of the syringe is at least substantially translucent, while the shield is substantially transparent and has a spaced series of indicia marked along at least a portion of the length thereof for use in determining, or measuring, the amount of liquid drawn through the hypodermic needle and into the barrel of the syringe.

The improved hypodermic syringe of this invention also includes an end shield formed integrally with the safety shield, at the second end thereof, for generally and fully enclosing the second end of the safety shield once the shield has been moved into its extended position to enclose the hypodermic needle within the shield.

The safety shield is maintained in the retracted position on the barrel by a first annular ring formed on the first end of the barrel and extending outwardly toward the safety shield, and a second annular ring formed on the interior of the first end of the safety shield and extending toward the first annular ring, both annular rings being yieldably engaged in a mechanical interlocking relationship with one another so that the second annular ring can be urged over the first annular ring as the safety shield is moved from the retracted into the extended position.

Intermediate the first and second ends of the safety shield, a series, in this instance, three, aligned protrusion are formed on the interior of the safety shield projecting inwardly toward, and into slidable engagement with, the barrel of the syringe for supporting the safety shield on the barrel for movement, for spacing the safety shield about the barrel of the syringe, and for locking the safety shield in its extended position.

Lastly, the improved hypodermic syringe of this invention includes a novel means for locking the safety shield in the extended position thereon, this novel means comprising a spaced series of locking slots formed transversely on the second end of the barrel with respect to the length thereof, the slots being spaced and sized to receive one each of the protrusions formed on the interior of the safety shield and slidably engaged with the barrel therein. The locking slots are formed on the exterior of the barrel, and each slot has a ramped surface over which the protrusions of the safety shield are passed. The ramped surfaces are constructed so that the ramped surface is compressed downwardly by the protrusion as it is passed thereover, the ramped surface springs back to its original shape to lock the protrusions in each locking slot, respectively, thereafter.

The protrusions on the safety shield are guided onto the locking slots by a spaced series of guide wedges formed in an alternating spaced series with the locking slots at the second end of the barrel, so that as the safety shield is grasped with the fingers of one hand, the fingers of the other hand grasping the grip flange of the barrel, the safety shield is moved from the retracted position to the extended position with a simple linear motion, the guide wedges ensuring that the protrusions are aligned with one each of the locking slots, the protrusions passing over the ramped surfaces of the each locking slot, and then downward into one each of the locking slots to lock the safety shield into position without the need to otherwise rotate the safety shield, or engage or disengage any threads thereon.

Accordingly, it is an object of the present invention to provide an improved hypodermic syringe with safety shield, and a method of using same, which provides a quick, simple, one step device and method for locking the safety shield into its extended position on the barrel of the hypodermic syringe.

Another object of the present invention is to provide an improved hypodermic syringe and safety shield, and method of using same, which is easy to use for encouraging syringe users to fully protect themselves from accidental needle sticks by moving the safety shield into its locked position.

Yet another object of the present invention is to provide an improved hypodermic syringe with safety shield that has a clear or transparent safety shield with markings or indicia thereon for ease of use in accurately measuring medicine and other fluids drawn into the syringe, and for dispensing fluids from the syringe.

Still another object of the present invention is to provide an improved hypodermic syringe with safety shield which provides a simple one piece safety shield which is constructed to completely enclose the hypodermic needle of a syringe after use.

An additional object of the present invention is to provide an improved hypodermic syringe with safety shield which will automatically align the protrusions on the safety shield with the locking slots on the barrel to ensure a quick, simple method of locking the safety shield on the barrel which will prevent accidental needle sticks while shielding the needle after use.

Still another object of the invention is to provide an improved hypodermic syringe with safety shield which is inexpensive to manufacture, is simple to use, and is durable and rugged in structure.

Accordingly, these, and other objects of the invention will be realized in the improved hypodermic syringe with safety shield, and method of using same, illustrated in FIGS. 1–7 hereof, and as disclosed more fully hereinbelow.

DETAILED DESCRIPTION

Figures 1, 2:
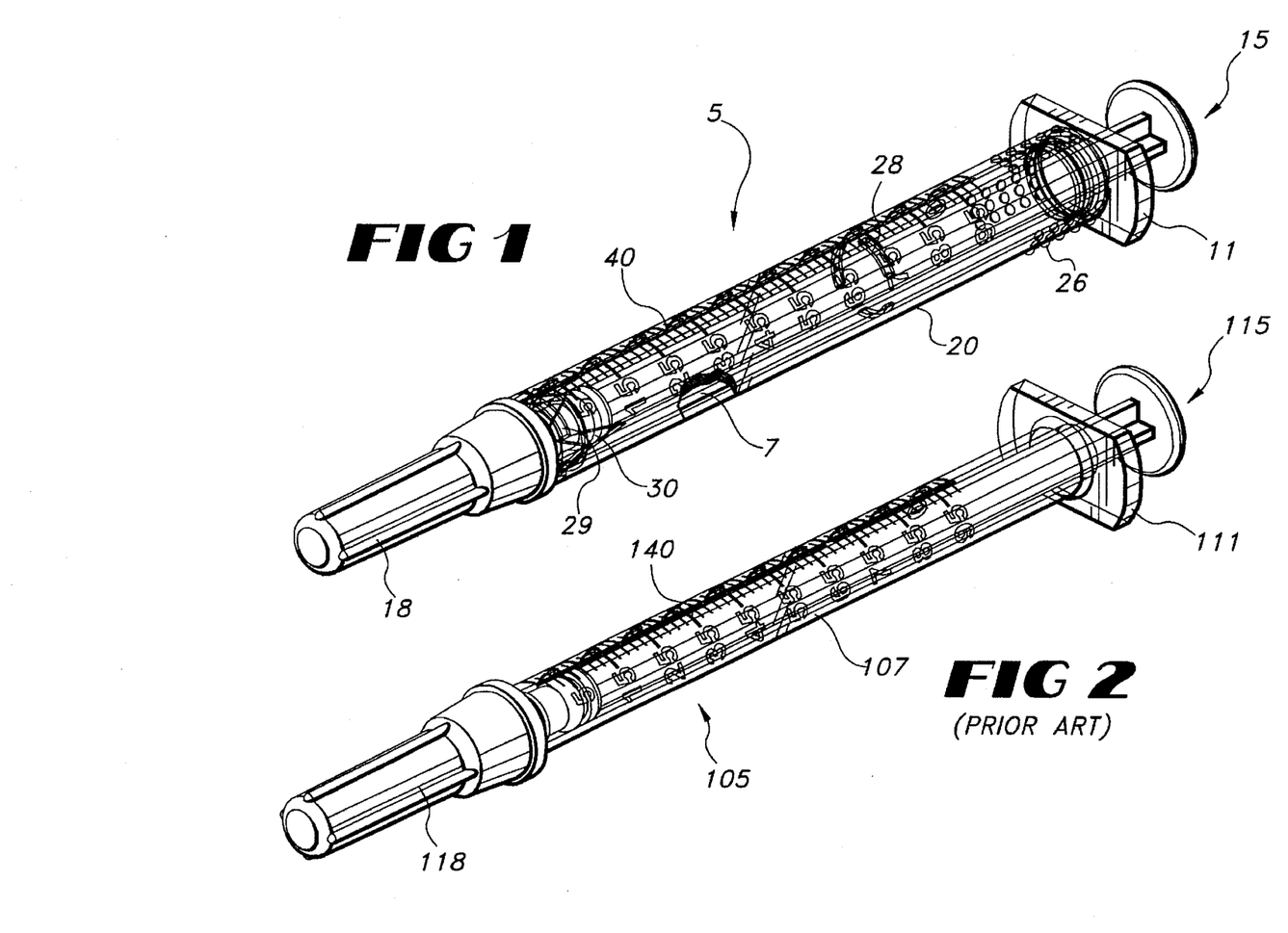
FIG. 1 is a perspective view of a preferred embodiment of the hypodermic syringe with safety shield of this invention showing the safety shield in the retracted position on the hypodermic syringe.
FIG. 2 is perspective view of a prior art hypodermic syringe without a safety shield.
Figure 3:
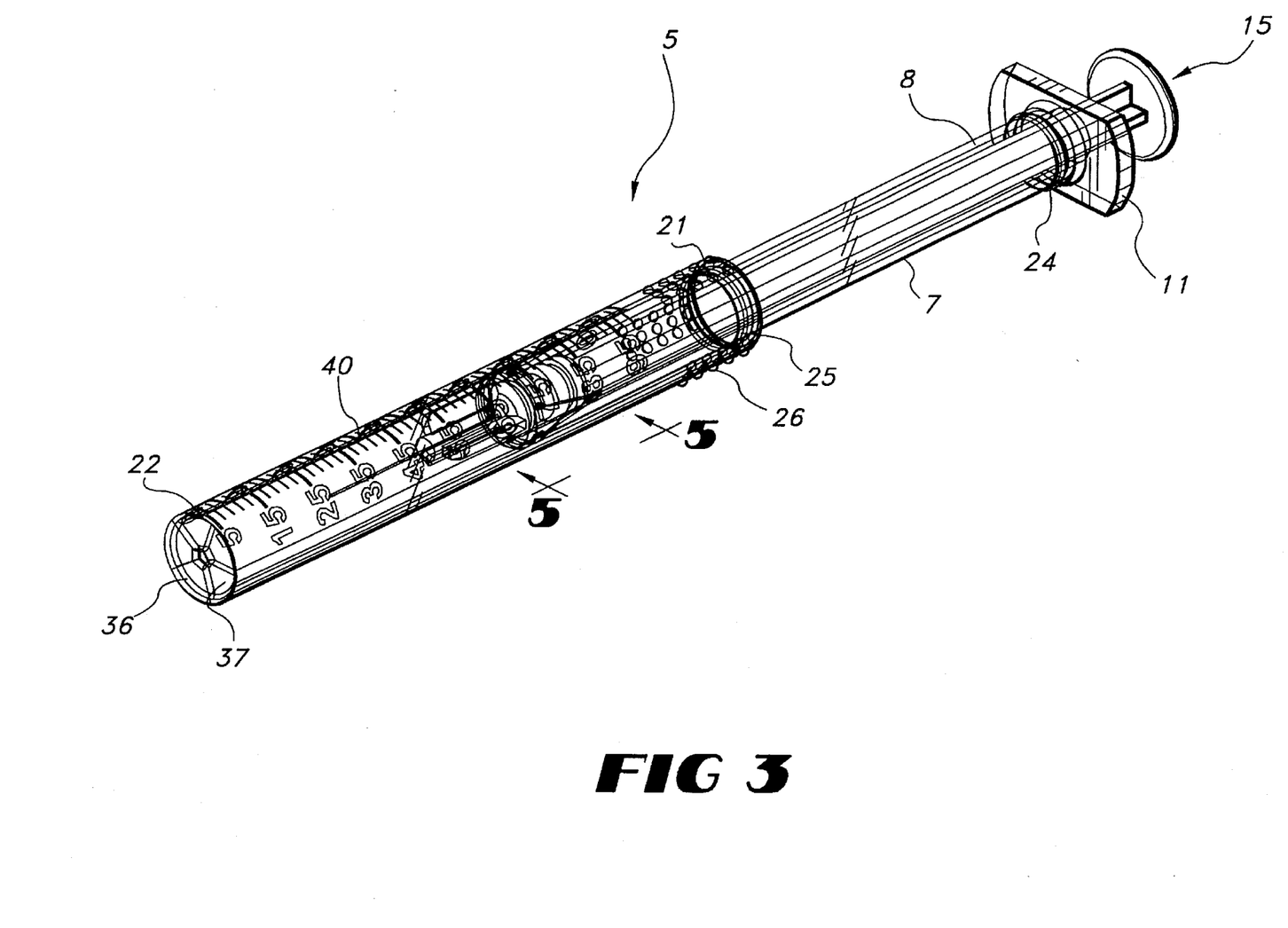
FIG. 3 is perspective view of the improved hypodermic syringe with safety shield of FIG. 1 shown in the extended or locked position on the barrel of the hypodermic syringe.
Figure 4:
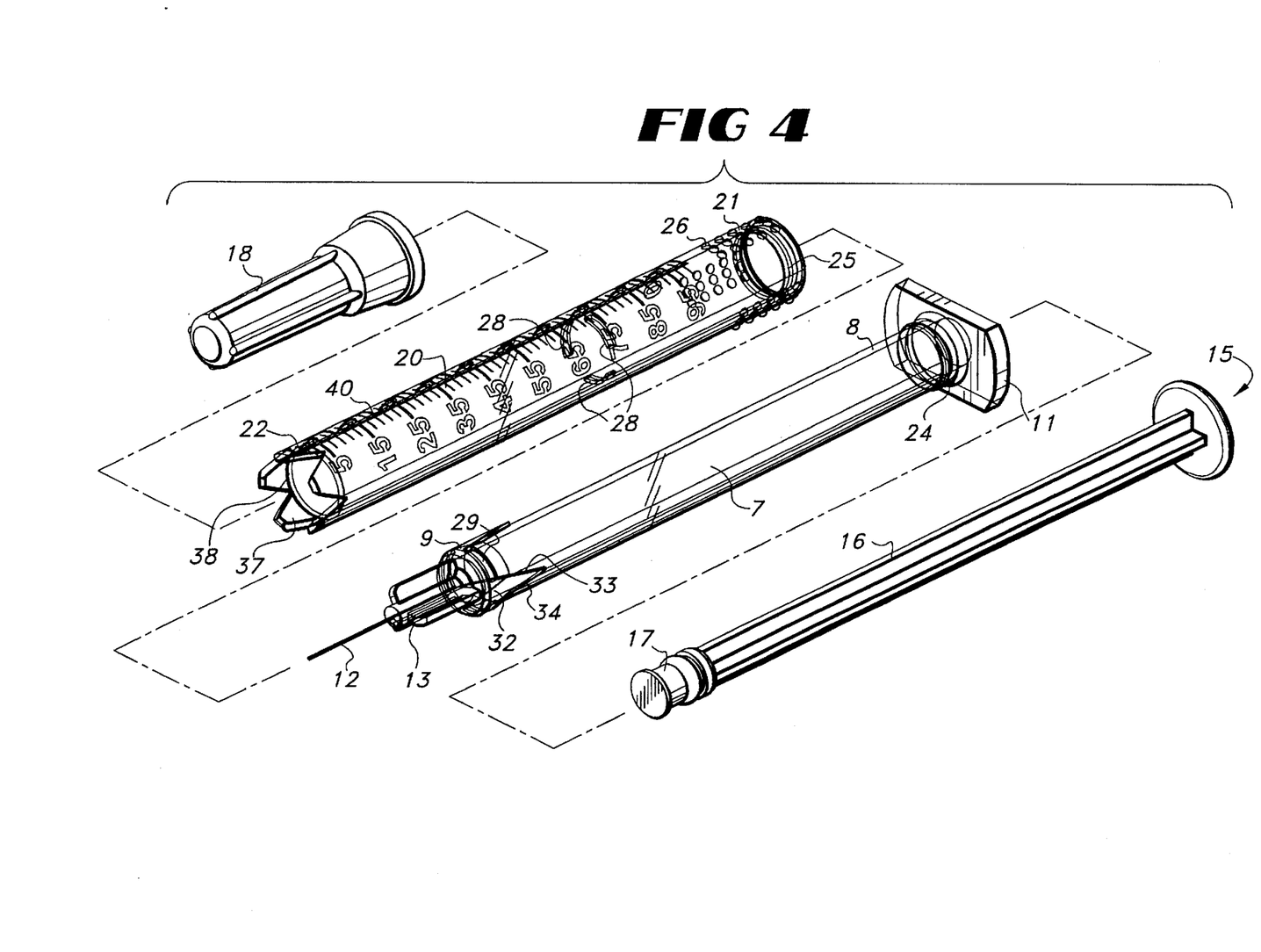
FIG. 4 is an exploded perspective view of the preferred embodiment of the hypodermic syringe with safety shield of FIG. 1.
Figure 5:
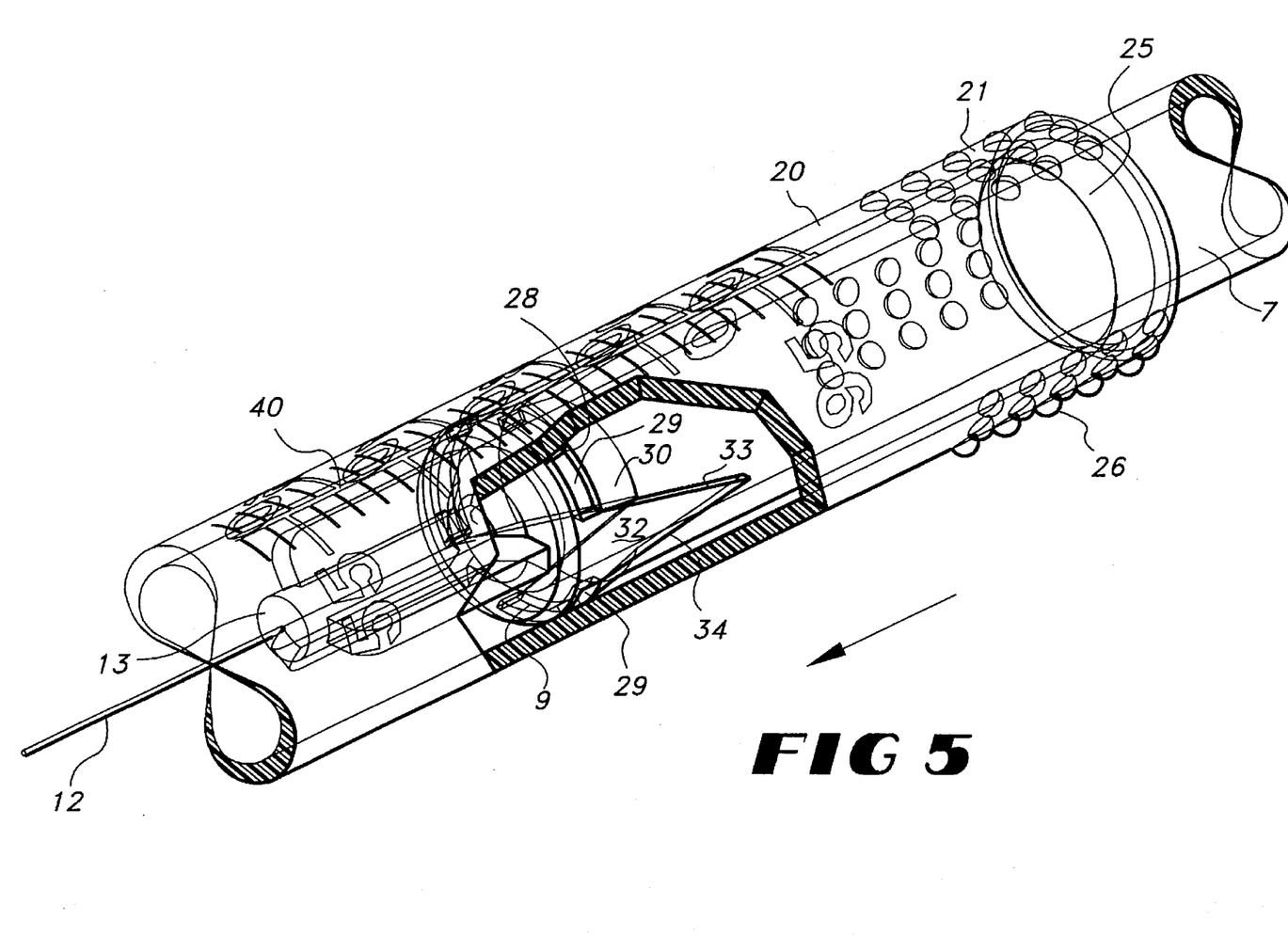
FIG. 5 is a partially cutaway partial view of the hypodermic syringe with safety shield of this invention along line 5—5 of FIG. 3.

Referring now to the drawings, in which like characters of reference indicate like parts throughout the several views, numeral 5 of FIGS. 1, 3, and 4 illustrates a preferred embodiment of the improved hypodermic syringe with safety shield of this invention.

As best shown in FIG. 4, hypodermic syringe 5 includes an elongated hollow, cylindrical barrel 7 having a first open end 8 and a spaced second closed end 9. A grip flange 11 is formed at the first end of the barrel in conventional fashion. A conventional hypodermic needle 12 is attached to second end 9 through a conventional needle hub, or luer, 13 formed as an integral part of barrel 7.

In known fashion, hypodermic syringe 5 includes a reciprocable plunger assembly 15 having an elongate plunger shaft 16 at the end of which is a plunger piston 17 sized and shaped of a flexible and resilient material for being sealed on the interior walls of barrel 7 in use. As shown in FIGS. 1 and 4, hypodermic syringe 5 is also provided with a needle cap or sheath 18 which is received over needle 12 to ensure the sterility of needle 12 prior to use, and to prevent accidental needle sticks prior to using hypodermic syringe 5.

Referring now to FIGS. 1, 3, and 4, hypodermic syringe 5 includes an elongate, hollow, cylindrical safety shield 20 positioned coaxially about barrel 7. Safety shield 20 has a first open end 21 and a spaced second open end 22. As shown in FIG. 1, safety shield 20 is in its retracted position so that needle 12 projects axially from the second end 9 of barrel 7, and is not enclosed or housed within safety shield 20. Safety shield 20 is shown in its extended or locked position in FIG. 3, in which the safety shield has been moved along the length of barrel 7, from the first end toward the second end thereof, to enclose needle 12 within the safety shield to prevent the accidental contact or touching of the needle.

A first continuous annular ring 24 is formed on the first end 8 of barrel 7. A corresponding second continuous annular ring 25 is formed on first end 21 of safety shield 20, each of the rings being constructed to be yieldably interlocked in mechanical engagement with one another in the retracted position of safety shield 20 shown in FIG. 1. It is anticipated that barrel 7 will be constructed of a relatively "soft" plastic, for example, polyethylene, whereas safety shield 20 may be constructed of the same plastic or a relatively more "rigid" plastic, for example, a polycarbonate resin or other similar material, so that as the safety shield is being moved into its extended position shown in FIG. 3, second annular ring 25 will press down and force first annular ring 24 to yield thereto, thus unlocking the safety shield from its retracted position and allowing it to slide along the length of barrel 7.

After being passed over first annular ring 24, second annular ring 25 serves to support safety shield 20 about barrel 7 while also spacing the safety shield from the exterior surface of barrel 7 and to minimize the frictional drag of the barrel on the safety shield as it is moved into its extended position. First end 21 of safety shield 20 is provided with a plurality, or spaced series, of raised grip knobs 26 so that when the safety shield is grasped between the fingers of a user, the grip knobs will help to ensure that the fingers of the person do not otherwise slip or accidentally move along safety shield 20 and come into accidental contact with needle 12.

Intermediate first end 21 and second end 22 of safety shield 20 is an aligned series of protrusions 28. Here three protrusions 28 are provided for the purposes of supporting safety shield 20 about barrel 7, spacing safety shield 20 from the barrel, and as the locking protrusions or tabs which will be received within locking slots 29 formed on the second end 9 of barrel 7. Although only three tabs 28 and three corresponding locking slots 29 are illustrated in FIGS. 1, 3–5, a greater, or perhaps lesser, number of locking tabs and slots may be used, as desired. It is also possible that protrusions 28 may comprise a continuous annular ring constructed in similar fashion to annular ring 25, and that locking slots 29 may be a continuous slot formed on the second end of barrel 7.

Here three elongated and transverse locking slots 29 are formed at the second end 9 of barrel 7, each of which corresponds in size and shape to each one of protrusions 28. Each one of locking slots 29 is provided with a ramped surface 30 which extends from the locking slot in the direction of, and toward, first end 8 of the barrel so that each one of protrusions 28, respectively, will pass over one of ramped surfaces 30, urging the softer material of the barrel, and thus the ramped surfaces, downward as the protrusions pass thereover, so that as the protrusions are received within locking slots 29, the softer plastic material of locking slots 29 and ramped surfaces 30 springs or extends upward to ensure that locking tabs/protrusions 28 are filly held within slots 29, thus ensuring that safety shield 20 remains in its locked and extended position.

As each of protrusions 28 is spaced equally apart from one another on the interior surface of safety shield 20, each one of locking slots 29 is spaced equally apart from one another about first end 9 of the barrel. Positioned intermediate each one of the locking slots at the second end of the barrel, so that they are spaced in alternating series with the locking slots, is a series of guide wedges 32. As there are three locking slots, therefore, there are three guide wedges 32 on the second end of the barrel. Each one of guide wedges 32 is generally triangular in shape having its wider base leg or portion extending along the periphery of second end 9 of the barrel, and having two angled surfaces, a first angled surface 33, and a second angled surface 34, extending in the direction from the second end toward the first end of the barrel for guiding protrusions 28 toward and into each one of locking slots 29.

Thus, when safety shield 20 is grasped with the fingers of one hand, and grip flange 11 is grasped with the fingers of the other hand, once second annular flange 25 has been passed over first annular flange 24 and the safety shield is moved toward the second end of the barrel, protrusions 28 will strike one of angled surfaces 33 or 34 so that the protrusions of the safety shield are aligned with one each of locking slots 29 and are received therein without the need to fully extend the safety shield into a first intermediate position, and then rotate the safety shield into a second or locked position as is common with the known safety syringes. Accordingly, this provides a much easier method of using the improved syringe of this invention as opposed to the other safety syringes known in the art, and thus lessens the chance of accidental needle sticks.

Figure 6:
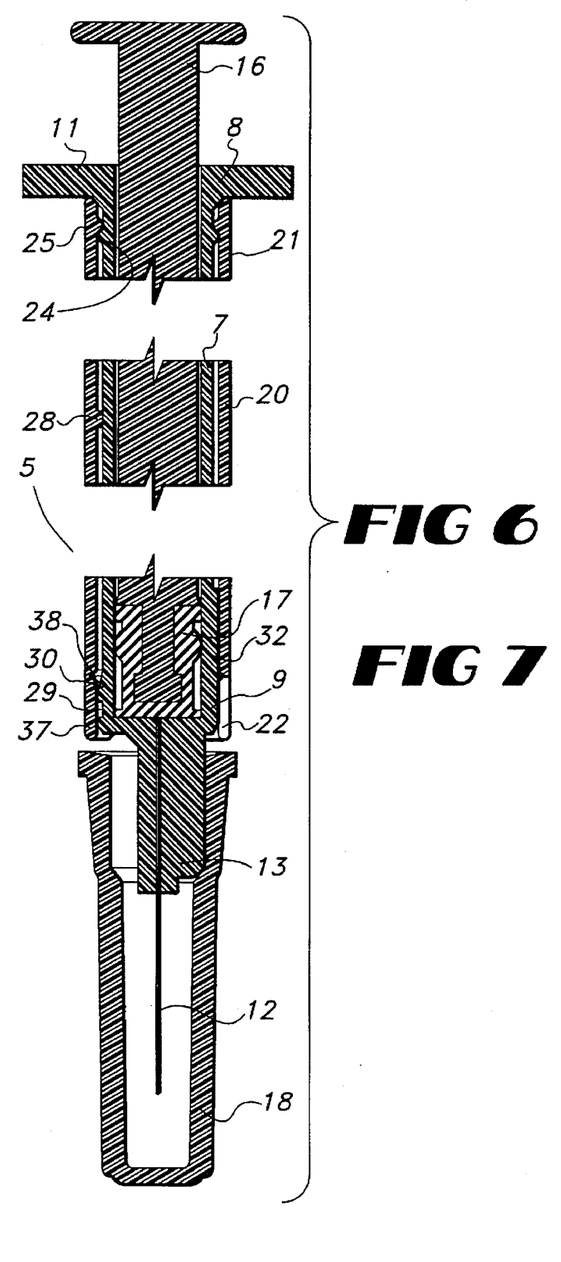
FIG. 6 is a side elevational view in cross-section of the hypodermic syringe with safety shield of FIG. 1 shown in the retracted position.

As shown in FIGS. 3 and 4, a unique feature of the safety shield of this invention is an integral end shield 36 formed as a part of the safety shield, and constructed to ensure that the safety shield can be completely enclosed about needle 12 after its use. As best shown in FIGS. 4 and 6, a spaced series of end shield segments 37 are provided at the second end 22 of safety shield 20. Each one of end shield segments 37 is generally arcuate or pie shaped, so that when moved into a closed position transverse to the length of safety shield 20, shown in FIG. 3, they form a consolidated end shield 36 which will enclose the second end of the safety shield. Each one of end shield segments 37, therefore, is formed along a score line 38 along the periphery of second end 22 of the safety shield, each one of end shield segments 37 being constructed for movement from an open position, as shown in FIG. 4, into the closed position of FIG. 3 in yieldable fashion.

It is anticipated that once end shield segments 37 are moved into their closed position they cannot be reopened so that the end shield cannot be otherwise opened to once again expose the second end 22 of the safety shield. Although not illustrated herein, it is anticipated that end shield segments 37 can be provided with side edge portions designed to overlap one another, respectively, and to interlock with one another. For example, a raised ridge and recessed groove could be provided in the opposed edge surfaces of each segment 37 to otherwise snap or lock the end shield segments into their closed position as shown in FIG. 3.

Figure 7:
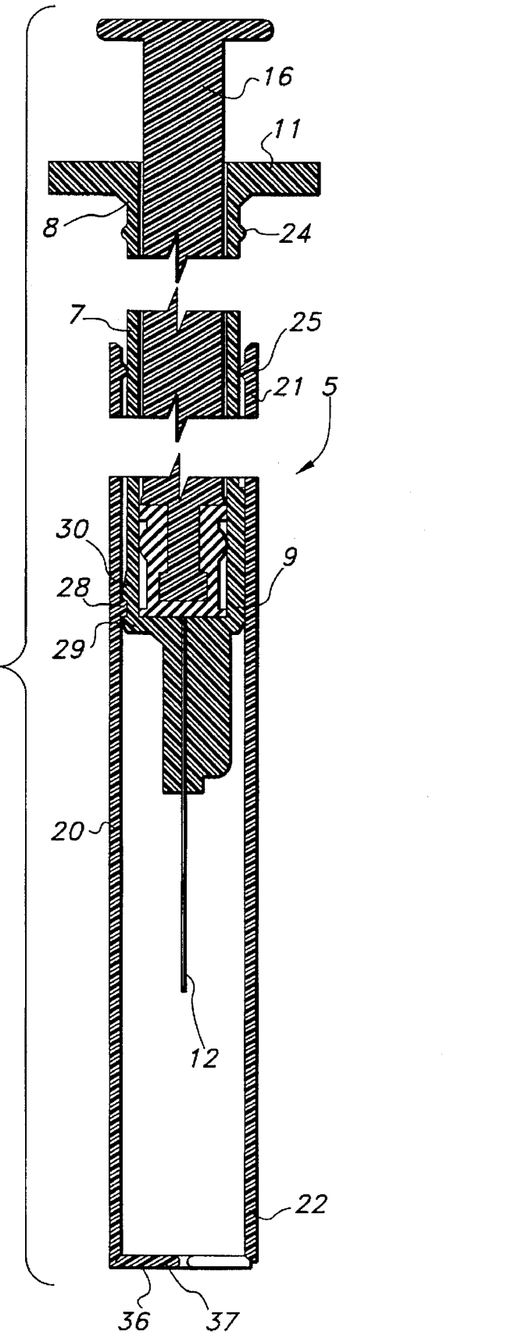
FIG. 7 is a side elevational cut-away view in cross-section of the hypodermic syringe with safety shield of FIG. 1 shown in the extended and locked position.

As shown in FIG. 6, therefore, when safety shield 20 is in its retracted position on barrel 7, end shield segments 37 extend coaxially about barrel 7 on second end 9 thereof, so that cap 18 can be received thereon to seal needle 12. Once the hypodermic syringe has been used, and safety shield 20 has been moved into its extended position, as shown in FIGS. 3 and 7, it is anticipated that the user can take safety shield 20 and place the second end 22 thereof against a hard surface and press the safety shield against the surface so that end shield segments 37 collapse along score line 38 into their closed position, as shown in FIG. 7, thus fully enclosing needle 12 within the safety shield.

Another unique feature of this invention is that rather than placing markings or indicia on the barrel 7 of the syringe, as is typically done and which would be otherwise obscured by safety shield 20, indicia 40 are provided along at least a portion of the length of safety shield 20 so that any fluid measurements are determined by looking at the safety shield and the underlying barrel, rather than having to look through the safety shield at the markings thereunder and on the barrel. Accordingly, it is anticipated that barrel 7 will be constructed of at least a substantially translucent material, for example polyethylene, whereas safety shield 20 will be constructed of a more transparent material, again a polycarbonate resin or other clear plastic, having sufficient flexibility to allow end shield segments 37 to be formed along score line 38 into their closed position, although safety shield could be constructed of polyethylene also, if so desired.

In contrast, to the improved hypodermic syringe with safety shield of this invention, a prior art hypodermic syringe 105 is illustrated in FIG. 2. Hypodermic syringe 105 has a barrel 107 with a grip flange 111 formed at one end, a plunger assembly 115 received through the open end and reciprocally moved within the barrel, and a cap 118 received at the other end on which a hypodermic needle (not illustrated) is received. A series of markings 140 are formed along the length of barrel 107, as is known in the art. Accordingly, when a conventional hypodermic syringe 105 is used with a safety shield, the safety shield is placed over the barrel and thus tends to obscure, to some extent, indicia 140, thus potentially impacting the accuracy of the fluid measurements being made by the health care professional, or other user, of hypodermic syringe 105. Thus, by marking indicia 40 along the length of safety shield 20, on the outside of barrel 7, greater accuracy is allowed in the use of hypodermic syringe 5.

OPERATION

The use of hypodermic syringe 5 is illustrated in FIGS. 1, 3, and particular FIGS. 6 and 7. Referring first to FIG. 6, which correlates with the retracted position of FIG. 1, safety syringe 20 is shown with second annular ring 25 received behind first annular ring 24 for retaining the safety shield in the retracted position. Each one of projections 28 protrudes inwardly from safety shield 20 and into slidable engagement with the exterior surface of barrel 7, thus supporting safety shield 20 coaxially about the barrel. Each one of end shield segments 37 is shown in its open position extending coaxially about barrel 7, and cap 18 is shown on the second end 9 of the barrel, the cap being received on the barrel to ensure sterilization of needle 12 prior to hypodermic syringe 5.

When it is desired to use hypodermic syringe 5, cap 18 is removed, and in known fashion, grip flange 11 is grasped between the fingers of the user, whereas the other fingers of the user will grasp plunger shaft 16 and withdraw plunger piston 17 backward for drawing fluid through hypodermic needle 12 into the hollow interior of barrel 7. As this is done indicia 40, FIGS. 1, 3, 4, and 5, are used to ensure that the correct mount of fluid is drawn through needle 12 and into barrel 7. Thereafter, and in known fashion, the hypodermic needle is introduced through the epidermis of a patient, for example when an injection is being given, whereupon plunger shaft 16 is actuated by moving plunger piston 17 toward the second end 9 of the barrel, thus expelling the fluid to be injected from inside the barrel through hypodermic needle 12 and into the patient.

Once the injection is completed, the health care professional or other user will continue to grasp grip flange 11 between the fingers of one hand, and will place the fingers of the other hand on raised grip knobs 26 formed at first end 21 of safety shield 20, and to move the safety shield from the first end 8 toward the second end 9 of the barrel. In so doing, second annular flange 25 will compress first annular flange 24 to release safety shield 20 from its retracted position for movement from first end 8 toward second end 9 of the barrel. Safety shield 20 is supported for movement on barrel 7 by protrusions 28, and second annular ring 25.

While being moved along the length of the barrel, the protrusions 28 may strike one of angled surfaces 33, 34 (FIG. 5) of guide wedges 32 if any misalignment of protrusions 28 with respect to locking slots 29 is present, rotating safety shield 20 to the necessary extent so that one each of protrusions 28 is aligned with each one of locking slots 29. Protrusions 28 are thus received on one each of ramped surfaces 30 and compress the ramped surfaces downward with respect to the safety shield as each one of protrusions 28 passes thereover. Protrusions 28 are then passed into each one of locking slots 29, respectively, whereupon the softer and more compressible plastic of the barrel expands upward to lock the safety shield in its extended position (FIG. 3) about needle 12. Thereafter, end shield segments 37 are folded or yielded along score line 38 (FIG. 7) so that the end shield 36 is moved into its closed position as shown in FIGS. 3 and 7.

While a preferred embodiment of the improved hypodermic syringe with safety shield of this invention has been disclosed in the foregoing specification, it is understood by those skilled in the art that variations and modifications thereof can be made without departing from the spirit and scope of the invention as set forth in the following claims. In addition, the corresponding structures, materials, acts, and equivalents of all means or step plus function elements in the claims below are intended to include any structure, material, or acts for performing the functions in combination with other claimed elements as specifically claimed herein.

We claim:

1. A hypodermic syringe for giving injections, said syringe comprising:

an elongated hollow cylindrical barrel with a first open end and a spaced second closed end, a grip flange formed at the first end of said barrel, a hypodermic needle attached to the second end of said barrel and extending axially away therefrom said needle being in sealed fluid communication with the hollow interior of said barrel, and a plunger assembly received within the barrel; and an elongated hollow cylindrical safety shield positioned coaxially about said barrel in a retracted position so that said needle projects axially out of said safety shield, said safety shield being constructed and arranged for movement on the barrel from said retracted position into an extended position in which the needle is housed within the safety shield, said safety shield being spaced closely from said barrel and having a first open end and a spaced second open end;

wherein said barrel is constructed to be at least substantially translucent and said safety shield is constructed to be substantially transparent;

wherein said safety shield has a spaced series of indicia marked along at least a portion of the length thereof with respect to the barrel in said retracted position for measuring the amount of liquid to be held within the barrel of the syringe for injection;

and wherein said safety shield further includes an end shield formed as a part of the second end thereof, said end shield being held in an open position in the retracted position of said safety shield, and being constructed and arranged to be yieldably moved from said open position into a second closed position on the second end of said safety shield in the extended position thereof for enclosing the hypodermic needle within the safety shield.

2. The syringe of claim 1, said end shield comprising a spaced plurality of end shield segments hingedly connected to the periphery of the second end of said safety shield, said end shield segments projecting away from the second end of the safety shield in said open position said end shield segments being constructed and arranged to yield for movement into a transverse position with respect to the length of the safety shield in said closed position for enclosing the needle housed within the safety shield.

3. The syringe of claim 1, further comprising means for retaining said safety shield in said retracted position on said barrel.

4. The syringe of claim 3, said means for retaining said safety shield in said retracted position comprising a first annular ring formed on the exterior of the first end of said barrel and extending outwardly of said barrel toward said safety shield, and a second annular ring formed on the interior of the first end of said safety shield and extending inwardly of said safety shield toward said barrel, said first and said second annular rings each being yieldably interlocked in mechanical engagement with one another.

5. The syringe of claim 1, said syringe further comprising means for locking said safety shield on the barrel in said extended position.

6. The syringe of claim 5, further comprising:

a plurality of spaced and generally aligned protrusions formed along the interior surface of said safety shield transversely with respect to the length thereof, said protrusions being positioned intermediate the first end and the second end of the safety shield and protruding from the safety shield into slidable engagement with the exterior of said barrel for movement along the length thereof and for spacing said safety shield from said barrel;

said means for locking said safety shield on the barrel in said extended position comprising a corresponding plurality of spaced slots sized and shaped to receive one each of said protrusions therein, said slots being formed on the exterior surface of the barrel at the second end thereof and having a ramped surface facing toward the second end of the barrel for allowing one each of said protrusions to pass thereover and into one of said slots; and means for guiding said protrusions toward one each of said slots as said safety shield is moved from said retracted position into said extended position.

7. A hypodermic syringe for giving injections, said syringe comprising:

an elongated hollow cylindrical barrel with a first open end and a spaced second closed end, a grip flange formed at the first end of said barrel, a hypodermic needle attached to the second end of said barrel and extending axially away therefrom, said needle being in fluid communication with the hollow interior of said barrel, and a plunger assembly received within the barrel;

an elongated hollow cylindrical safety shield positioned coaxially about said barrel, said safety shield being constructed and arranged for movement on the barrel from a retracted position in which the needle projects axially out of the safety shield into an extended position in which the needle is housed within the safety shield, the safety shield being spaced closely from said barrel and having a first open end and a spaced second open end;

means for retaining said safety shield in said retracted position, said means for retaining comprising a first annular ring formed on the exterior of the first end of the barrel and extending outwardly of the barrel toward the safety shield and a second annular ring formed on the interior of the first end of the safety shield and extending inwardly of the safety shield toward the barrel, said first and said second annular rings each being yieldably interlocked in mechanical engagement with one another; and means for locking said safety shield on the barrel in said extended position.

8. The syringe of claim 7, further comprising a plurality of spaced and generally aligned protrusions formed along the interior surface of said safety shield transversely with respect to the length thereof, said protrusions being positioned intermediate the first end and the second end of the safety shield and protruding from the safety shield into slidable engagement with the exterior of said barrel for movement along the length thereof and for spacing said safety shield from said barrel, said means for locking said safety shield on the barrel in said extended position comprising a corresponding plurality of slots sized and shaped to receive one each of said protrusions therein, said slots being formed on the exterior surface of the barrel at the second end thereof and having a ramped surface facing toward the first end of the barrel for allowing one each of said protrusions to pass thereover and into one of said slots.

9. The syringe of claim 8, further comprising means for guiding said protrusions toward one each of said slots as said safety shield is moved from said retracted position into said extended position.

10. The syringe of claim 9, said means for guiding said protrusions comprising a plurality of spaced guide wedges formed on the exterior of the second end of the barrel with respect to said slots, said guide wedges being spaced in alternating series with said slots about said barrel and extending from the second end thereof beyond the ramped surfaces of said slots toward the first end of the barrel for guiding said protrusions toward said ramped surfaces.

11. The syringe of claim 8, each of said protrusions being sized and shaped to yieldably pass over one each of said ramped surfaces and into one each of said slots.

12. The syringe of claim 7, wherein said barrel is constructed to be at least substantially translucent and said safety shield is constructed to be substantially transparent, said safety shield having a spaced series of indicia marked along at least a portion of the length thereof for measuring the amount of liquid within the barrel of the syringe.

13. The syringe of claim 7, further comprising a plurality of raised grip knobs formed on the exterior of the first end of said safety shield for use as a hand grip in moving said safety shield from said retracted position into said extended position.

14. The syringe of claim 7, further comprising means, formed integrally with said safety shield, for enclosing the second end of the safety shield once the safety shield has been moved into said extended position.

15. A hypodermic syringe for giving injections, said syringe comprising:

an elongated hollow cylindrical barrel with a first open end and a spaced second closed end, a grip flange formed at the first end of said barrel, a hypodermic needle attached to the second end of said barrel and extending axially away therefrom, said needle being in fluid communication with the hollow interior of said barrel, and a plunger assembly received within the barrel;

an elongated hollow cylindrical safety shield positioned coaxially about said barrel, said safety shield being constructed and arranged for movement on the barrel from a retracted position in which the needle projects axially out of the safety shield into an extended position in which the needle is housed within the safety shield, the safety shield being spaced closely from said barrel and having a first open end and a spaced second open end;

a plurality of aligned protrusions formed along the interior surface of said safety shield transversely with respect to the length thereof, said protrusions being positioned intermediate the first end and the second end of the safety shield and extending from the safety shield into slidable engagement with the exterior of said barrel, said protrusions being constructed and arranged to slide along at least a portion of the length of the barrel and for spacing said safety shield from said barrel;

means for retaining said safety shield in said retracted position on said barrel; and means for locking said safety shield on the barrel in said extended position, said means for locking comprising a plurality of spaced slots sized and shaped to receive one each of said protrusions therein, said slots being formed on the exterior surface of the barrel at the second end thereof and having a ramped surface facing toward the first end of the barrel for allowing one each of said protrusions to pass thereover and into one of said slots.

16. The syringe of claim 15, said means for retaining said safety shield in said retracted position comprising a first annular ring formed on the exterior of the first end of the barrel and extending outwardly of the barrel toward the safety shield and a second annular ring formed on the interior of the first end of the safety shield and extending inwardly of the safety shield toward the barrel, wherein said first and said second annular rings are each sized and shaped to be yieldably interlocked in mechanical engagement with one another.

17. The syringe of claim 15, wherein said barrel is constructed to be at least substantially translucent and said safety shield is constructed to be substantially transparent, said safety shield having a spaced series of indicia marked along at least a portion of the length thereof for measuring the amount of liquid to be held within the barrel of the syringe for injection.

18. The syringe of claim 15, further comprising means, formed integrally with said safety shield, for enclosing the second end of the safety shield once the safety shield has been moved from said retracted position.

19. The syringe of claim 15, further comprising means for guiding said protrusions toward one each of said slots as said safety shield is moved from said retracted position into said extended position.

20. The syringe of claim 19, said means for guiding said protrusions comprising a plurality of spaced guide wedges formed on the exterior of the second end of the barrel with respect to said slots, said guide wedges being spaced in alternating series with said slots about the barrel and extending from the second end of the barrel beyond the ramped surfaces of said slots toward the first end of the barrel for guiding said protrusions toward said ramped surfaces.

21. A hypodermic syringe for giving injections, said syringe comprising:

an elongated hollow cylindrical barrel with a first open end and a spaced second closed end, a grip flange formed at the first end of said barrel, a hypodermic needle attached to the second end of said barrel and extending axially away therefrom, said needle being in fluid communication with the hollow interior of said barrel, and a plunger assembly received within the barrel;

an elongated hollow cylindrical safety shield positioned coaxially about said barrel, said safety shield being constructed and arranged for movement on the barrel from a retracted position in which the needle projects axially out of the safety shield into an extended position in which the needle is housed within the safety shield, the safety shield being spaced closely from said barrel and having a first open end and a spaced second open end;

a plurality of aligned protrusions formed along the interior surface of said safety shield transversely with respect to the length thereof, said protrusions being positioned intermediate the first end and the second end of the safety shield and protruding from the safety shield into slidable engagement with the exterior of said barrel, said protrusions being constructed and arranged for movement along the length of the barrel and for spacing the safety shield from the barrel;

means for retaining said safety shield in said retracted position on said barrel, said means for retaining comprising a first annular ring formed on the exterior of the first end of the barrel and extending outwardly of the barrel toward the safety shield, a second annular ring formed on the interior of the first end of the safety shield and extending inwardly of the safety shield toward the barrel, said first and said second annular rings being sized and shaped to be yieldably interlocked in mechanical engagement with each other;

means for locking said safety shield on the barrel in said extended position, said means for locking comprising a plurality of spaced slots sized and shaped to receive one each of said protrusions therein, said slots being formed on the exterior surface of the barrel at the second end thereof and having a ramped surface facing toward the first end of the barrel; and a plurality of spaced guide wedges formed in alternating series with said slots about the second end of the barrel for guiding said protrusions toward one each of said slots as said safety shield is moved from said retracted position into said extended position;

wherein said barrel is constructed to be at least substantially translucent and said safety shield is constructed to be substantially transparent, said safety shield having a spaced series of indicia marked thereon along at least a portion of the length thereof for measuring the amount of liquid to be held within the barrel of the syringe for injection.

22. A method of using a hypodermic syringe, the syringe having an elongated hollow cylindrical and generally translucent barrel with a first open end and a spaced second closed end, a grip flange formed at the first end of said barrel for being held between the fingers, the hypodermic needle being in sealed fluid communication with the hollow interior of the barrel and extending from the second end thereof, and a plunger assembly received within the barrel, said method comprising the steps of:

positioning an elongated hollow substantially transparent cylindrical safety shield having a first open end and a spaced second open end coaxially about the barrel in a retracted position in which the needle projects axially from said shield;

providing a spaced series of indicia marked along at least a portion of the length of said safety shield for measuring the amount of liquid to be drawn through the needle into the barrel for injection;

drawing the liquid to be injected by moving the plunger within the barrel from the second end toward the first end of the barrel;

moving said safety shield at least partially along the length of the barrel of the syringe from said retracted position into an extended position so that the hypodermic needle is housed within said safety shield; and yieldably moving an end shield formed as a part of the second end of the safety shield from a first open position on the safety shield into a second closed position on the second end of the safety shield, and enclosing the hypodermic needle within the second end of the safety shield in response thereto.

23. The method of claim 22, further comprising the steps of:

grasping the grip flange of the barrel between the fingers of one hand;

grasping a spaced series of grip knobs formed on the exterior of the first end of the safety shield with the fingers of the other hand;

releasing a first annular ring formed on the exterior of the first end of the barrel and extending outwardly of the barrel toward the safety shield from being yieldably and mechanically interlocked with a second annular ring formed on the interior of the first end of the safety shield and extending inwardly of the safety shield toward the barrel;

moving the first end of the safety shield toward the second end of the barrel into said extended position in response thereto; and locking said safety shield on the barrel and about the needle in response to moving said safety shield into said extended position.

24. The method of claim 23, wherein the step of moving the safety shield into said extended position includes the steps of:

providing a plurality of aligned protrusions along the interior surface of said safety shield transversely with respect to the length, and intermediate the first and the second ends thereof, said protrusions being in slidable engagement with the exterior of said barrel;

providing a plurality of spaced slots sized and shaped to receive one each of said protrusions therein, said slots being formed on the exterior surface of the barrel at the second end thereof and having a ramped surface facing toward the first end of the barrel;

providing a plurality of spaced guide wedges formed in alternating series with said slots about the second end of the barrel; and:

guiding said protrusions toward one each of said slots with said guide wedges in response to moving said safety shield from said retracted position into said extended position.

25. The method of claim 22, the step of enclosing the second end of the safety shield with said end shield further comprising the steps of moving a spaced plurality of end shield segments hingedly connected to the periphery of the second end of said safety shield from an open position on the second end of said safety shield in said retracted position into a transverse closed position with respect to the length of the safety shield in said extended position.

26. A hypodermic syringe for giving injections, said syringe comprising:

an elongated hollow cylindrical barrel with a first open end and a spaced second closed end, a grip flange formed at the first end of said barrel, a hypodermic needle attached to the second end of said barrel and extending axially away therefrom, said needle being in fluid communication with the hollow interior of said barrel, and a plunger assembly received within the barrel;

an elongated hollow cylindrical safety shield positioned coaxially about said barrel in a retracted position so that said needle projects axially out of said safety shield, said safety shield being constructed and arranged for movement on the barrel from said retracted position into an extended position in which the needle is housed within the safety shield, said safety shield being spaced closely from said barrel and having a first open end and a spaced second open end; and a spaced series of raised grip knobs formed on the exterior of the first end of said safety shield for use as a hand grip in moving said safety shield from said retracted position into said extended position;

wherein said barrel is constructed to be at least substantially translucent and said safety shield is constructed to be substantially transparent;

and wherein said safety shield has a spaced series of indicia marked along at least a portion of the length thereof with respect to the barrel in said retracted position for measuring the amount of liquid to be held within the barrel of the syringe for injection.

* * * * *

UNITED STATES PATENT AND TRADEMARK OFFICE
CERTIFICATE OF CORRECTION

PATENT NO : 5,651,774
DATED : July 29, 1997
INVENTOR(S): William J. Taranto & Norman C. Maarschalkerweerd It is certified that error appears in the above-identified patent and that said Letters Patent is hereby corrected as shown below:

In the Abstract, line 17, change the reference numeral "(4)" to -- (40) --.

Column 7, line 6, change "filly" to -- fully --.

Column 8, line 29, after the phrase "In contrast" at the beginning of the line, delete the comma.

Column 8, line 51, after the phrase "3, and" at the beginning of the line, insert -- in --.

Column 9, line 3, change "mount" to -- amount --.

Column 9, line 15, after the phrase "safety shield 20, and" delete the word "to."

Signed and Sealed this

Twenty-third Day of December, 1997

Attest:

BRUCE LEHMAN

Attesting Officer

Commissioner of Patents and Trademarks